(12) United States Patent
Lee et al.

(10) Patent No.: US 8,501,488 B2
(45) Date of Patent: Aug. 6, 2013

(54) COMPOUND FOR DERIVATIZING POLYPEPTIDES AND METHOD FOR SEQUENCING AND QUANTIFYING AMINO ACIDS IN POLYPEPTIDES USING THE SAME

(75) Inventors: Sang-Won Lee, Seoul (KR); Yong-Ho Lee, Incheon (KR)

(73) Assignee: Korea University Industry and Academy Cooperation Foundation, Seoul (KR)

( * ) Notice: Subject to any disclaimer, the term of this patent is extended or adjusted under 35 U.S.C. 154(b) by 1536 days.

(21) Appl. No.: 11/630,625

(22) PCT Filed: Jun. 29, 2005

(86) PCT No.: PCT/KR2005/002044
§ 371 (c)(1),
(2), (4) Date: Mar. 3, 2008

(87) PCT Pub. No.: WO2006/004341
PCT Pub. Date: Jan. 12, 2006

(65) Prior Publication Data
US 2008/0220483 A1     Sep. 11, 2008

(30) Foreign Application Priority Data

Jun. 30, 2004   (KR) .................. 10-2004-0050751

(51) Int. Cl.
*C07C 331/28*     (2006.01)
*G01N 33/00*      (2006.01)

(52) U.S. Cl.
USPC .............................................. 436/90; 558/17

(58) Field of Classification Search
USPC ............................................ 558/17; 436/90
See application file for complete search history.

(56) References Cited

U.S. PATENT DOCUMENTS 4,153,416 A * 5/1979 Bonner et al. .................. 436/57

OTHER PUBLICATIONS

Guillaume et al., "Differentially isotope-coded N-terminal protein suphonation: Combining protein identification and quantification", Proteomics 2006, 6, 2338-2349.*
Chen, P., et al., "De novo sequencing of tryptic peptides sulfonated by 4-sulfophenyl isothiocyanate for unambiguous protein identification using post-source decay matrix-assisted laser desorption/ionization mass spectrometry", Rapid Communications in Mass Spectrometry, vol. 18, 2004, pp. 191-198.
Bailey, G., et al., "Automated Sequencing of Insoluble Peptides Using Detergent", The Journal of Biological Chemistry, vol. 252, No. 7, Apr. 10, 1977, pp. 2218-2225.
Gao, J., et al., "Determination of the Effective Charge of a Protein in Solution by Capillary Electrophoresis", Proc. Natl. Acad. Sci., vol. 91, Dec. 1994, pp. 12027-12030.
Berger, S., et al., "High-Throughput Global Peptide Proteomic Analysis by Combining Stable Isotope Amino Acid Labeling and Data-Dependent Multiplexed-MS/MS", Anal. Chem., vol. 74, Oct. 1, 2002, pp. 4994-5000.
Gygi, S., et al., "Quantitative analysis of complex protein mixtures using isotope-coded affinity tags", Nature Biotechnology, vol. 17, Oct. 1999, pp. 994-999.
English translation of International Preliminary Examination Report dated Jun. 19, 2006, for PCT/KR2005/002044, indicating relevance of cited references.

* cited by examiner

*Primary Examiner* — Peter G O Sullivan
(74) *Attorney, Agent, or Firm* — Christie, Parker & Hale, LLP

(57) ABSTRACT

The present invention relates to a compound for N-terminal substitution of polypeptides which is used in sequencing and quantifying amino acids and a method for sequencing and quantifying an amino acid sequence using the same. The method for sequencing and quantifying amino acids in accordance with the present invention leads to a relative quantitative analysis of proteins with very high reliability, and can distinctively discriminate between y-type ions and b-type ions on the MS/MS spectra, providing the means for realization of high-reliability protein identification.

8 Claims, 5 Drawing Sheets

COMPOUND FOR DERIVATIZING POLYPEPTIDES AND METHOD FOR SEQUENCING AND QUANTIFYING AMINO ACIDS IN POLYPEPTIDES USING THE SAME

CROSS-REFERENCE TO RELATED APPLICATION

This application is a National Phase Patent Application of International Application Number PCT/KR2005/002044, filed on Jun. 29, 2005, which claims priority of Korean Patent Application Number 10-2004-0050751, filed on Jun. 30, 2004.

TECHNICAL FIELD

The present invention relates to proteomics, and more particularly to a compound that derivatizes the peptides by sulfonating their N-terminus, which is used in identifying and quantifying proteins, and a method for sequencing and quantifying amino acids in polypeptides using the same.

BACKGROUND ART

Proteomics refers to a diverse area of study including mass spectrometric analysis of proteins, products of genes, mapping of inter-relationship therebetween, and structural analyses of proteins, thereby ultimately elucidating functions of specific protein and genes thereof. Based on the studies of protein structures and roless of functional proteins expressed in genetic codes, determining the primary structures, or the amino acid sequences, of proteins should be the primary goal in proteomics research, since it provides necessary information for analyses of the tertiary structures of proteins.

A classical method for protein sequencing involves the use of Edman reagent, for example Edman degradation. This method is performed by reacting the N-terminus of proteins or peptides with phenyl isothiocyanate under basic conditions and then converting the reaction conditions into an acidic condition, to remove one amino acid in the form of thiazoline from the N-terminus. Therefore, it is possible to determine the entire sequence of proteins or peptides by analyzing amino acids on a stepwise basis. However, such a method is disadvantageous in that it requires high purity proteins or peptides for analysis, and is time consuming. Although recently, an auto sequencer that automatically repeats the above-mentioned reaction process has been developed, it takes from 30 minutes to one hour to determine one amino acid sequence and there is also a problem associated with a need for a large amount of sample when long amino acid sequence analyses are required, because desired products are not obtained in a yield of 100% by one cycle.

For these reasons, in 1980's, a method for analyzing proteins or peptide sequences using a mass spectrometer was introduced to overcome disadvantages associated with the use of Edman degradation. This method is called tandem mass spectrometry (referred to as tandem MS, hereinafter), and analyzes samples ions according to their mass-to-charge ratios, fragments an ion of interest by kinetic collision with inert gas such as helium. Observations of the resulting fragmented ions provide information for proteomic analyses of the proteins.

Conventionally, applications of the tandem MS technique in a peptide analysis result in the generation of daughter ions due to cleavages of certain peptide bonds, which are observed in a daughter-ion mass spectrum. Then, based on the comparison to well-established databases of known proteins, the sample is characterized. However, this method not only leads to erroneous results when the database is incorrect, even when the database is correct, results do not ensure absolute reliability because they are merely the probability that the identified peptide is indeed the desired one. As a result, a variety of attempts have been made to identify proteins by reducing the dependence on databases and mainly focusing on mass analysis results. When analyzing pure peptides using a tandem MS, most peptides exhibit complicated tandem mass spectra, so attempts have been made to simplify spectra by modifying with a series of treatments. As such, a method to directly obtain an amino acid sequence by means of tandem MS, without any database, is called de novo sequencing.

WO 02/08767 discloses a technique wherein chlorosulfonylacetyl chloride is used to sulfonate the N-terminus of a polypeptide, neutralizing b-type ions, which are the N-terminal fragments, so that only the y-type ions can be observed. However, this method suffers from problems in that chlorosulfonylacetyl chloride is over reactive and has two reactive sites, resulting in complex products, and furthermore, the method is completely inapplicable to quantification analyses. Also, since a lysine modification reagent also reacts with the epsilon amino groups of lysine side-chains, this method cannot be used for peptides with lysine at the C-terminus, placing a severe limitation on the utility of this technique.

In order to solve the above-mentioned problems, there have been efforts to protect the epsilon amino groups of the lysine side-chain prior to their sulfonation and also to convert lysine into homo arginine using O-methyl isourea to enhance ionization efficiency. However, these attempts may result in a significant loss of peptides due to the addition of one pretreatment step and also pose a problem that O-methyl isourea might react with the amino group of the N-terminus of the peptide.

Meanwhile, in order to further simplify interpretation of a tandem mass spectrum and to gain more useful information, techniques involving isotopic substitution have been developed.

Smith et. al. (*Analytical Chemistry*, Vol. 74, No. 19, Oct. 1, 2002) present a technique capable of simplifying interpretation of a tandem mass spectrum. According to the technique, yeasts are cultured in a medium containing $^{13}C$ isotope-labeled lysine (the 6 carbon atoms constituting lysine are substituted with $^{13}C$) and a medium containing untreated lysine, respectively, and the obtained cultures are mixed. Then the mixture is hydrolyzed using a proteolytic enzyme, Lys-C and the resulting products are allowed to discriminate between y-type and b-type, thus realizing simplification of the tandem mass spectrum. However, this method utilizes in vivo labeling and thus is not applicable to experiments involving human subjects, or when the orgasms subject to analyses have alternate routes to producing lysine in vivo. In addition, various attempts have been made to design methods capable of simultaneously performing protein identifications and quantification analyses. Gygi et. al. (*Nature Biotechnology*, Vol. 17, October 1999: 994-999) present quantitative analyses of complex protein mixtures using Isotope-Coded Affinity Tags (ICAT) in which H was substituted with D as the reagent. However, the reagent reacts with the thiol group of cysteine, while cysteine is only present in the amount of from 5 to 10% of total amino acids in most proteins. Therefore, this quantitative analysis using the reagent ICAT and cysteine inevitably exhibits significant error. In addition, due to the difference in the hydrogen-bond strengths between H and D, there is also a difference in retention time during reverse phase liquid chromatography. These factors result in the occurrence of errors in a quantification analysis, leading to pronounced lowering of reliability.

DISCLOSURE

Technical Problem

Therefore, the present invention has been made in view of the above problems, and the objects of the present invention are to provide a compound for N-terminal substitution of polypeptides capable of simultaneous identification and quantification of polypeptides with high reliability, and also to provide a method to sequence and quantify the amino acids using the compound.

Technical Solution

In accordance with an aspect of the present invention, the above and other objects can be accomplished by the provision of a compound for N-terminal substitution of polypeptides having Formula 1 which is used in a method for sequencing and quantifying amino acids in polypeptides by utilizing mass spectrometry.

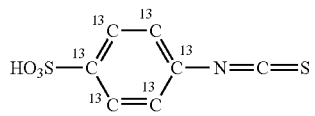

Formula 1

In accordance with another aspect of the present invention, there is provided a method for sequencing and quantifying amino acids in polypeptides, comprising:

(a) degrading each of the two polypeptide samples using proteolytic enzymes to obtain two oligo peptide mixtures, where the C-terminus of each oligo peptide is arginine or lysine;

(b) derivatizing one of the mixtures of the oligo peptide having arginine or lysine at the C-terminus with a compound for N-terminal substitution containing $^{12}C$ or $^{32}S$ or both, and derivatizing the other one of the oligo peptide mixture with a compound for N-terminal substitution containing $^{13}C$ or $^{33}S$ or both;

(c) mixing two derivatized oligo peptide mixtures and subjecting them to Reverse-Phase Liquid Chromatography (referred to as RPLC hereinafter);

(d) obtaining a base peak chromatogram and MS/MS spectra using a mass spectrometer; and (e) interpreting the obtained results.

In accordance with one embodiment of the present invention, the proteolytic enzyme may be trypsin, endoproteinase Lys C or endoproteinase Arg C.

In accordance with another embodiment of the present invention, the proteolytic enzyme is preferably trypsin.

In accordance with a further embodiment of the present invention, the compounds for N-terminal substitution containing $^{12}C$ or $^{32}S$ or both are compounds represented by Formula 2, and the compounds for N-terminal substitution containing $^{13}C$ or $^{33}S$ or both may be isotope compounds in which a portion or all of $^{12}C$ and $^{32}S$ are substituted with $^{13}C$ and $^{33}S$, respectively, while maintaining the same structural formula as the compounds for N-terminal substitution containing $^{12}C$ or $^{32}S$ or both.

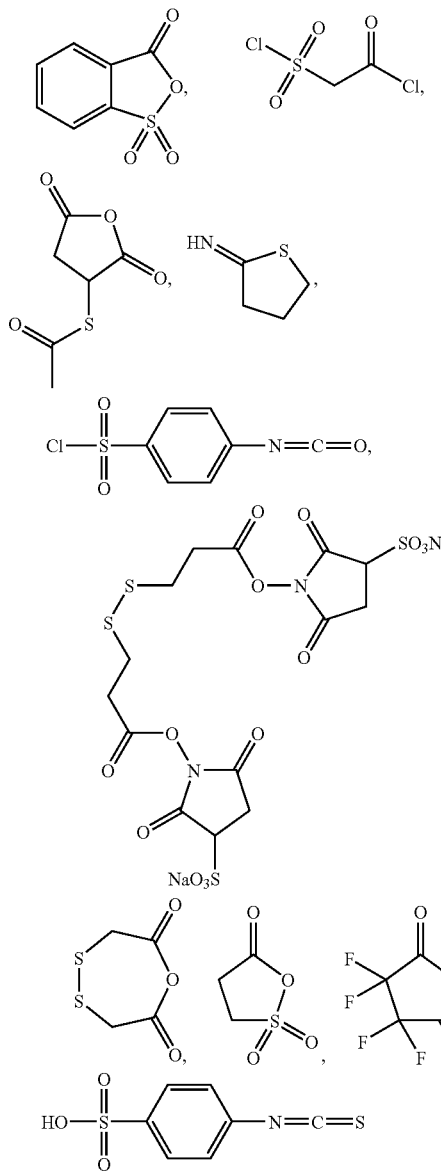

Formula 2

In addition, preferably, the compound for N-terminal substitution containing $^{12}C$ is a compound having Formula 3, and the compound for N-terminal substitution containing $^{13}C$ is an isotope compound in which $^{12}C$ in the compound of Formula 3 is substituted with $^{13}C$.

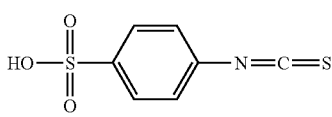

Formula 3

In accordance with the present invention, the mass spectrometer may be a Matrix-Assisted Laser Desorption/Ionization (referred to as MALDI, hereinafter) type mass spectrometer.

In accordance with further embodiment of the present invention, the mass spectrometer may be an Electro Spray Ionization (referred to as ESI, hereinafter) type mass spectrometer and may be directly connected to the RPLC.

Preferably, the pH value in step (b) is in the range of 7 to 9.

In addition, the step of derivatizing lysine is preferably carried out by only derivatizing the N-terminus of lysine, while keeping the epsilon-amino group of lysine intact.

In accordance with the preferred embodiment of the present invention, step (e) may be carried out using commercially available software programs or databases.

DESCRIPTION OF THE DRAWINGS

The above and other objects, features and other advantages of the present invention will be more clearly understood from the following detailed description taken in conjunction with the accompanying drawings, in which.

BEST MODE

Figure 1:
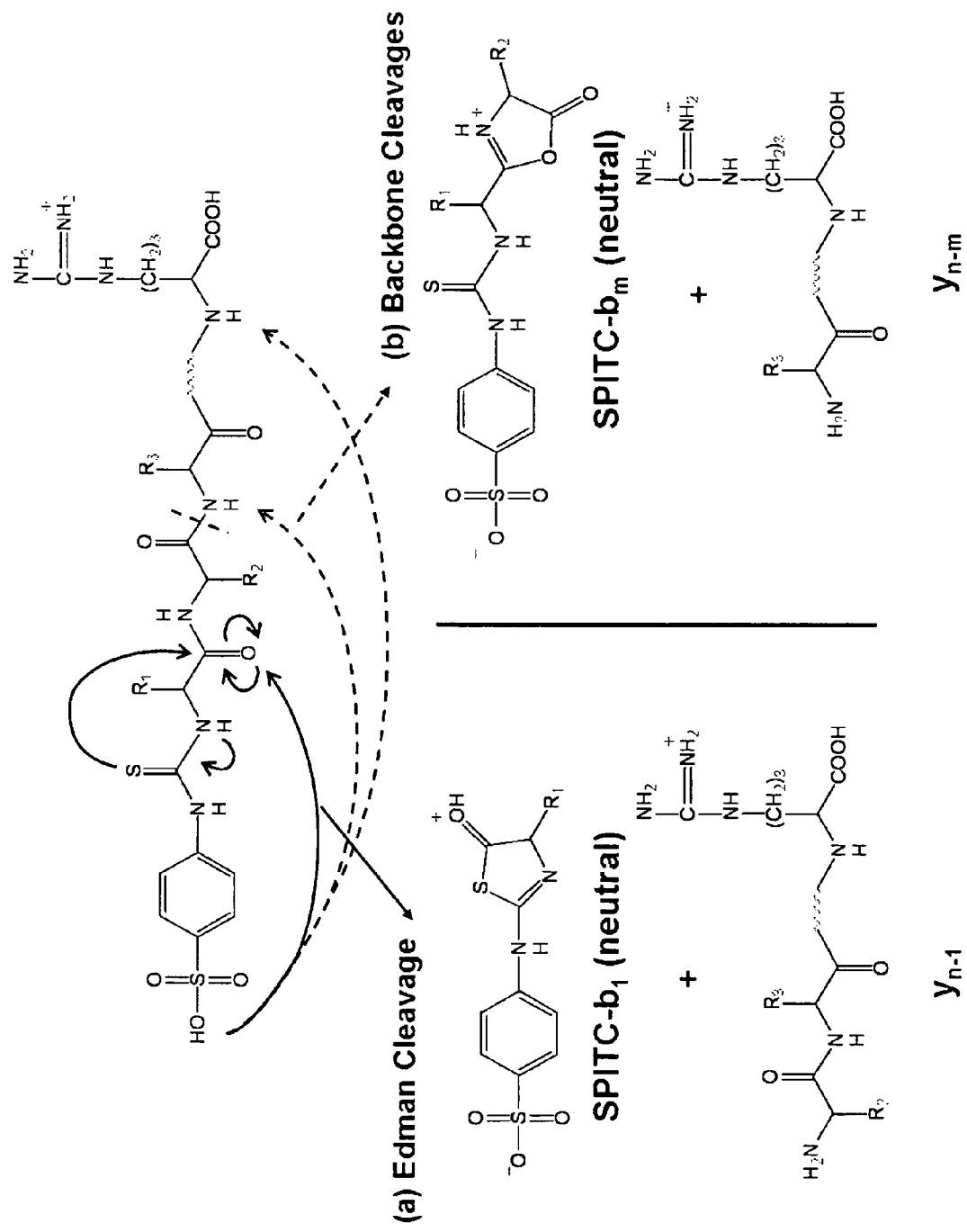
FIG. 1 schematically shows a degradation mechanism in the case of obtaining MS/MS spectra in accordance with the present invention.

Now, the present invention will be described more in detail.

As used herein, the term "polypeptide" refers to a molecular chain consisting of more than 500 amino acids linked via peptide bonds, and the term "oligo peptide" refers to a peptide with a smaller number of amino acids, for example, greater than 2 to less than 500 amino acids linked via peptide bonds.

As used herein, the term "fragments" refers to species formed by cleavages of the N-terminus, C-terminus or both termini of polypeptides, and the term "label" refers to species that bind to the termini of oligo peptides to derivatize them.

In accordance with the present invention, the compound for N-terminal substitution, which is used in a method of analyzing and quantifying amino acid sequences of polypeptides utilizing mass spectrometry, is substituted at the N-terminus of an oligo peptide, and the carbon atoms or sulfur atoms present in that compound are substituted with isotopes to impose mass differences allowing de novo sequencing and also relative quantitative analyses of proteins in experimental and control groups. The compound for N-terminal substitution utilizable in the present invention may react with the N-terminus of oligo peptides, and is not particularly limited so long as the resulting species in the gas phase contain functional groups capable of providing the oligo peptide with $H^+$. For example, compounds exemplified by Formula 2 may be used as the compound for N-terminal substitution.

Compounds produced by reactions of the compounds listed in Formula 2 with the N-terminus of an oligo peptide (ASHLGLAR) are the following compounds of Formulae I through IX:

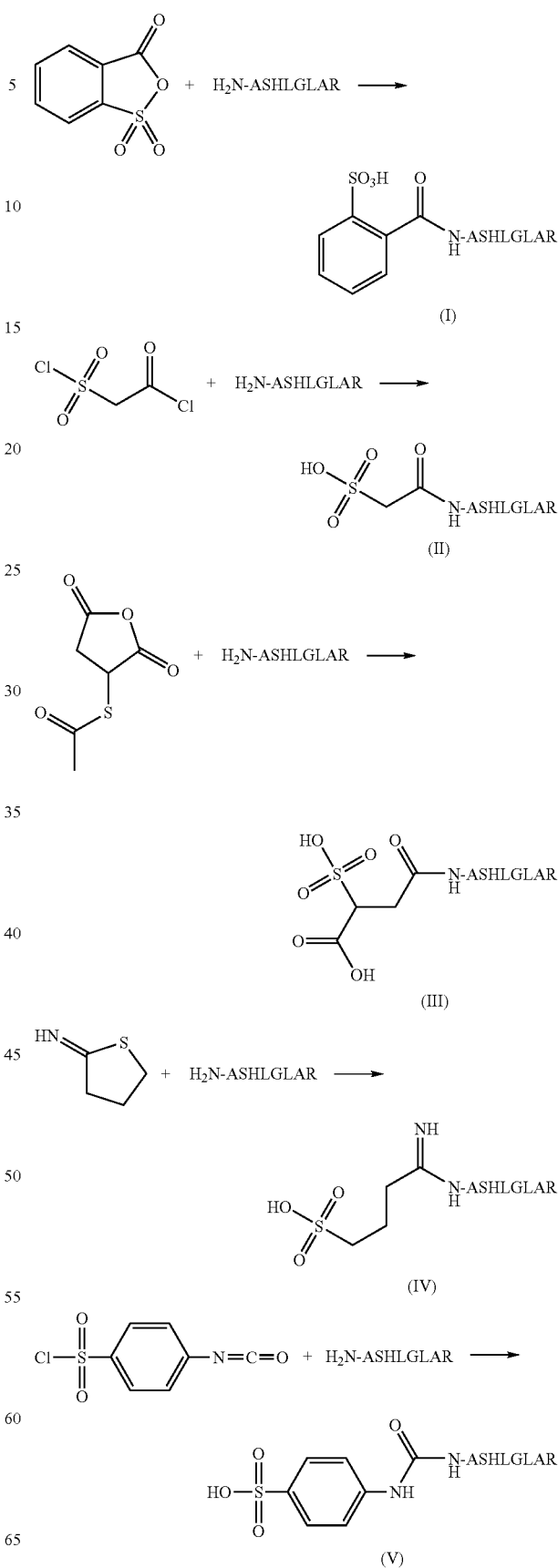

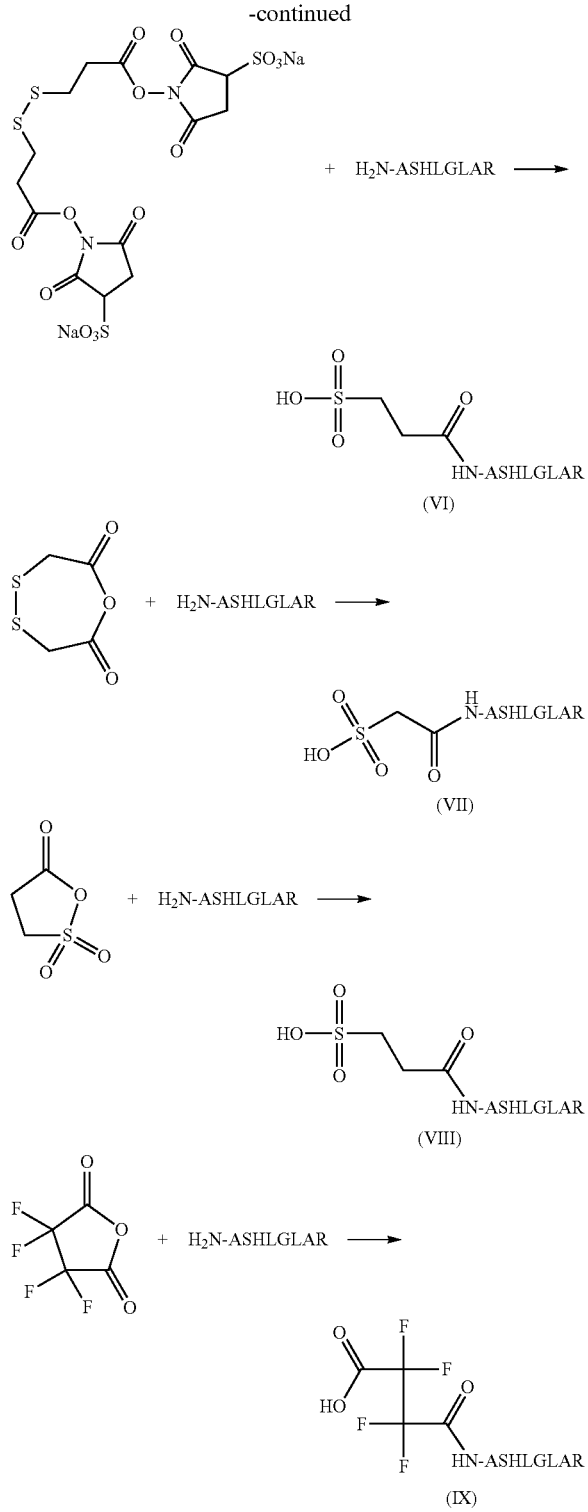

Except for the compound in Formula IX, all of the compounds have a sulfonic acid group ($HSO_3^-$). Since compound IX contains no $HSO_3^-$ group, and is highly acidic, the compound in the gas phase can provide the oligo peptide with $H^+$. Meanwhile, in the case of compounds IV, VI and VII, after reactions of the corresponding compounds with the oligo peptide, terminal SH groups of resulting species are oxidized using oxidizing agents such as $H_2O_2$, forming the $HSO_3^-$ group. In the case of compound III, after the reaction of the corresponding compound with the oligo peptide, a thioester group is hydrolyzed to form a thiol group, which is then oxidized to form the $HSO_3^-$ group, using the oxidizing agents such as $H_2O_2$.

In accordance with the preferred embodiment of the present invention, $^{12}$C6-4-Sulphophenyl isothiocyanate (referred to as $^{12}$C-SPITC hereinafter) of Formula 3 may be employed as the compound for N-terminal substitution and the isotopically labeled compound is $^{13}$C6-4-Sulphophenyl isothiocyanate (referred to as $^{13}$C-SPITC hereinafter). The $^{13}$C-SPITC is a compound wherein each of the 6 carbon atoms present in the phenyl ring of 4-Sulphophenyl isothiocyanate is substituted with $^{13}$C, and is very suitable for de novo sequencing of amino acid sequences in proteins as well as for relative quantitative analyses of proteins for experimental and control groups.

The present invention employs the combined use of $^{12}$C-SPITC and $^{13}$C-SPITC. Two samples are separately reacted with $^{12}$C-SPITC and $^{13}$C-SPITC to derivatize the N-termini of peptides, thereby obtaining separately labeled peptide samples. Then, the obtained samples are mixed and are subjected to mass spectrometry in order to rapidly acquire a variety of information with high reliability.

The SPITC has only one thiocarbonyl group capable of reacting with the amine group of the peptide, and exhibits good selectivity for such a reactive site, which can be further improved by controlling reaction conditions. Therefore, even in the case of peptides containing lysine residues, the SPITC is minimally reactive with the epsilon-amino group of lysine, and may be allowed to selectively react with the amino group of the N-terminus. Therefore protection of the epsilon-amino group of lysine is not necessary.

FIG. 1 schematically shows a degradation mechanism in the case of obtaining MS/MS spectra in accordance with the present invention. In principle, Edman degradation, as previously described, refers to the cleavage of one amino acid of the N-terminus using the Edman reagent, phenyl isothiocyanate (PITC), in the bulk phase, but it is known that a similar type of degradation also occurs even in the gas phase (Journal of the American Society for Mass Spectrometry 2001, 12, 288-295). As shown in FIG. 1a, Edman degradation, as used hereinafter, refers to cleavage of one amino acid at the N-terminus in the form of thiazoline by the action of S of the thiocarbonyl group as a nucleophile in the gas phase. Accordingly, in the case of the SPITC-oligo peptide having a +1 charge, the chemical species resulting from Edman degradation may be represented by SPITC-$b_1$ (neutral), and chemical species at the C-terminus may be represented by $y_{n-1}$.

Meanwhile, when $^{12}$C-SPITC and $^{13}$C-SPITC utilized in the present invention derivatize the N-terminus of the peptide, a backbone cleavage, as shown in FIG. 1b, occurs in addition to Edman degradation. This is because the sulfonyl group of SPITC is highly acidic, thus acting as an $H^+$ source, and the $H^+$ transfers to the oxygen of the carbonyl group, activating the carbonyl group, which leads to degradation. In the case of the SPITC-oligo peptide having a +1 charge, species resulting from the backbone cleavage are SPITC-$b_m$ (neutral) at the N-terminus and $y_{n-m}$ at the C-terminus. As a result, MS/MS spectral analysis products in accordance with the present invention include fragments generated by backbone cleavage, as well as Edman degradation products, and fragments generated by Edman degradation, among them, form major peaks. Meanwhile, when the C-terminus of the oligo peptide is lysine, lysine exhibits proton affinity smaller than arginine and thus proton transfer tends to occur easily. Therefore, the produced $y_{n-1}$ ions undergo internal degradation and thereby b ions, to which the SPITC is not bound, may be detected.

Meanwhile, since SPITC-$b_1$ (neutral) and SPITC-$b_m$ (neutral), produced as a result of the degradation of the SPITC-oligo peptide with a +1 charge, are not detected in MS/MS spectra, and in general, only y-type ions appear on the spectrum, use of the compound for N-terminal substitution in accordance with the present invention simplifies peaks of the spectrum, thus enabling efficient interpretation thereof.

In accordance with the present invention, when a mass spectrum of oligo peptide with a +1 charge is obtained after preparing the respective isotope-labeled oligo peptides by degradation of two protein samples for each experimental and control group using proteolytic enzymes, and derivatization of the N-termini of the resulting protein degradation products using $^{13}$C-SPITC and $^{12}$C-SPITC, the obtained spectrum exhibits paired peaks, or the doublets, that are 6 Da apart and the peak at the greater mass value corresponds to $^{13}$C-SPITC derivatized-oligo peptide. Meanwhile, it is possible to quantify a relative quantity of the oligo peptide corresponding to the above-mentioned peaks, based on the comparison of the sum of intensity between the respective peaks during elution of the doublet.

Next, when MS/MS spectra of the above doublet are obtained, fragments in the form of SPITC-b are neutral and thus do not appear on the spectra, while the charged y-type ions are present. However, if highly basic amino acids such as histidine are at the N-terminus, b-type ions may occasionally appear. In this case, due to the co-existence of y-type and b-type ions, interpretation of peaks may be difficult with conventional means, but, in accordance with the present invention, the b-type ions accompany the partner peaks exhibiting a 6-Da mass difference and thus it is possible to easily distinguish the b-type ions from the y-type ions.

Meanwhile, when the oligo peptide has a +2 charge, a doublet exhibiting a 3-Da difference in mass appears in spectrum and it is possible to quantify the relative quantity of the oligo peptide corresponding to the above-mentioned peaks in the doublet based on comparison of the intensity between the peaks.

In the MS/MS spectrum, the peak for the doubly charged b-type ions are also shown along with those from the y-type ions, and the overall peak patterns become complex. However, since the b-type ions accompany their partner peaks exhibiting a 6-Da difference in mass it is possible to discriminate b-type from y-type ions $^{13}$C-SPITC, as described above, may be prepared as follows. First, concentrated sulfuric acid is added to $^{13}$C-substituted aniline s to sulfonate the para position. The resulting $^{13}$C-sulfanilic acid is mixed with thiophosgene for reaction with the amine group of the sulfanilic acid, leading to the formation of $^{13}$C-4-sulfophenyl isothiocyanate.

The method for sequencing and quantifying amino acids in polypeptides in accordance with the present invention comprises: (a) degrading each of the two polypeptide samples using proteolytic enzymes to obtain two oligo peptide mixtures, where the C-terminus of each polypeptide is arginine or lysine; (b) derivatizing one mixture of the oligo peptide having arginine or lysine at the C-terminus with a compound for N-terminal substitution containing $^{12}$C or $^{32}$S or both, and derivatizing the other with a compound for N-terminal substitution containing $^{13}$C or $^{33}$S or both; (c) mixing two derivatized oligo peptide mixtures and subjecting them to Reverse-Phase Liquid Chromatography; (d) obtaining a base peak chromatogram and MS/MS spectra using a mass spectrometer; and (e) interpreting the obtained results for de novo sequencings of polypeptides by simple treatment and at the same time, determine relative quantification of experimental and control proteins with high reliability. That is, the method in the present invention suggests that it is possible to realize protein identification with higher reliability and to obtain relatively high protein quantification efficiency by derivatization of the N-terminus of the oligo peptide using only one reagent.

The protein identification technique in the present invention is referred to as a bottom up approach, which requires a pretreatment process involving cleaving proteins into oligo peptides having suitable sizes using proteolytic enzymes prior to protein sample analyses. Concersely, there is a top down approach, which is widely employed for performing high-resolution MS such as Fourier Transform Ion Cyclotron Resonance (FT-ICR). According to this method, the protein to be mass-analyzed is not subject to any treatment prior to the mass analysis, and the protein corresponding to a desired mass is trapped in an Inductive Coupled Plasma Cell (ICR cell), followed by degradation of protein using an external source (electrons, light), thus facilitating protein identification by observing the daughter ions from protein degradation. This method has an advantage of process simplicity, but requires highly pure proteins because contaminants may cause false identifications.

When degrading the protein using proteolytic enzymes in step (a) of the present invention, the reason why the oligo peptide has to have arginine (R) or lysine (K) at the C-terminus is that arginine is the most basic of all the amino acids, with lysine being the second most basic. Amino acids with high basicity have greater tendencies to trap $H^+$ and the protonated forms of these amino acids can be easily detected in the mass spectrometer. Although there is no particular limit to proteolytic enzymes utilizable in the present invention, trypsin, endoproteinase Lys C, and endoproteinase Arg C are preferred because, when proteins are degraded by one of these enzymes, the C-terminus of the resulting oligo peptides is either arginine or lysine. However, the most preferred is trypsin because it is inexpensive and provides excellent degradation efficiency when used for protein degradation. An oligo peptide degraded by trypsin is referred to as a tryptic peptide.

Among various ionization schemes, in two of the more widely used methods for protein analyses are MALDI and ESI, and either one may be incorporated into the equipment setup presented in the current invention as long as they are conventionally designed for experiments in the proteomics field. Ionization by the MALDI process is not a very effective means for protonation of peptides, so detection of the peptides whose terminal amino acid is lysine is inefficient compared to the results obtained by ESI mass spectrometry. Prior to a mass analysis, due to the presence of oligo peptides that cannot be identified by mass spectrometry alone, peptides are subject to RPLC, which separates the peptides based on their hydrophobicity differences. The RPLC system is directly connected to the mass spectrometer so that the liquid from the system is ionized in the gas phase by means of ESI. In contrast, MALDI performs ionization of the solid-phase sample to the gas phase and thus cannot be directly connected to the liquid chromatography system. Furthermore, it is also troublesome in that the eluate from liquid chromatography should be collected at predetermined intervals and analyzed separately.

In connection with the method for sequencing and quantifying amino acids in polypeptides as described, the pH value in step (b) should be within the range of 7 to 9, in order to control the selectivity of SPITC for reaction. The reason is that the lysine-terminated tryptic peptide contains two amino groups, and only within this pH range, it is guaranteed that only the amino group in the backbone reacts with the SPITC and the epsilon-amino group does not undergo reactions with SPITC to a substantial extent. If the pH value is less than 7, $H^+$ is bound to the amino groups and the nucleophilicity becomes too low to initiate the reaction. Conversely, if the pH value is greater than 9, the epsilon-amino group also undesirably participates in the reaction.

As the final step, interpretations of the spectrum, base peak chromatogram, and MS/MS spectra are carried out using commercially available software programs or databases, which are not particularly limited so long as they are conventionally utilized in the proteomics field. The present invention uses SEQUEST (ThermoFinnigan).

Conventional ICAT reacts with cysteine only, which inevitably lowers reliability of quantified data, while the present invention performs quantification with all the tryptic peptides derived from various types of proteins, significantly reducing statistical errors and leading to remarkably high reliability.

It is a common practice to obtain MS data from the base peak chromatography, where the abscissa represents time and the ordinate represents intensity. The chromatogram shows peaks from the ions with the strongest intensity, measured at an arbitrary point in time, in the mass spectrum, and furthermore, the mass spectrum is recovered when the chromatogram is viewed from the z-axis direction.

Mode for Invention

EXAMPLES

Now, the present invention will be described more in detail with reference to the following Examples. These examples are provided only for illustrating the present invention and should not be construed as limiting the scope and spirit of the present invention.

Example 1

1-1. Preparation of $^{13}$C-Sulfanilic Acid 4 ml of concentrated sulfuric acid was added dropwise to $^{13}$C-substituted aniline (1 ml, 10 mmol) (Aldrich) in an ice bath and the resulting product was heated to the temperature of 180 to 190° C. for 6 hours, cooled at the room temperature, and added to cold water. The precipitates thus obtained were filtered and washed with cold water to obtain a solid product. The product was then dissolved in boiling water, decolorized with activated carbon, immediately filtered, and crystallized at 4° C. 600 mg of $^{13}$C-sulfanilic acid (yield: 32%) was obtained as the final product when the crystal was dried under a vacuum.

$^1$H NMR ($D_2O$, 300 MHz): δ 7.28 ppm (doublet 2H, J=8.7 Hz), δ 7.72 ppm (doublet, 2H, J=8.7 Hz)
ESI-MS (negative mode): m/z=172 Da ([M−H]$^-$)

1-2. Preparation of $^{13}$C-4-Sulfophenyl Isothiocyanate 100 mg (0.58 mmol) of the 13C-sulfanilic acid in 5.3 ml of 3M HCl acid was mixed with a 67% (v/v) solution (0.38 ml, 3.28 mmol) of thiophosgene in carbon tetrachloride, and the mixture was vigorously stirred for 12 hours at the room temperature. AcOEt was used to remove moisture from the resulting mixture, and the remaining product was dried with $MgSO_4$, and filtered. The filtrate was concentrated under reduced pressure to obtain an oily residue and a 0.5 M $NaHCO_3$ solution (1.2 ml) was added and to neutralize the residue. The resulting material was freeze-dried to obtain 118 mg (yield: 86%) of the sodium salt of $^{13}$C-4-sulfophenyl isothiocyanate.

$^1$H NMR ($D_2O$, 300 MHz): δ 7.26 ppm (doublet 2H, J=8.7 Hz), δ 7.64 ppm (doublet, 2H, J=8.7 Hz)
ESI-MS (negative mode): m/z=214 Da ([M−H]$^-$)
FT-IR: 2085 cm$^{-1}$ (N=C=S group's stretching mode)

Preparative Example 1

1-1. Preparation of Oligo Peptide Sample

In order to test whether $^{12}$C-SPITC and $^{13}$C-SPITC quantitatively respond to oligo peptides, 10 nmol of anaphylatoxin C3a fragment 70-77 (ASHLGLAR) was dissolved in 5 μl of a 1:1 pyridine/water solution to prepare an oligo peptide solution (A).

1-2. Derivatization of Oligo Peptide 1 mg of a reagent in which $^{12}$C-SPITC and $^{13}$C-SPITC prepared in Example 1 were mixed in a 1:1 mol ratio was dissolved in 200 μl of a pyridine/water/ethanol (1:1:2) solution to prepare a mixed stock solution of $^{12}$C-SPITC and $^{13}$C-SPITC immediately before use. The prepared oligo peptide solution (A) was mixed with 5 μl of a mixed stock solution of $^{12}$C-SPITC and $^{13}$C-SPITC and the pH value of the resulting oligo peptide-SPITC solution was adjusted to about 8. The solution was reacted at 50° C. for one hour while gradually stirring with an Eppendorf thermomixer (Brinkmann Instruments). Then the solution was completely evaporated in a high-speed vacuum concentrator and the resulting product was dissolved in 5 μl aqueous solution of 0.05% trifluoro acetic acid (referred to as TFA hereinafter) and 0.2% acetic acid. Then the mixture was micro-demineralized using a micro column, which was home-built by packing a PEEK tube (manufactured by Upchurch Scientific) with the length of 4 cm and the inner diameter of 400 μm with branched hydrocarbon particles (pore size: 300, and particle size: 5 μm, manufactured by Phenomenex) containing 18 carbon atoms. The micro-demineralization was carried out by loading 5 μl of the peptide solution into the micro column using a 6-port switching valve (manufactured by Valco International), washing the column with 100 μl of an aqueous solution of 0.05% TFA and 0.2% acetic acid, followed by development using 100 μl of acetonitrile. The resulting product was thoroughly dried in a high-speed vacuum concentrator and stored at −20° C. for subsequent experiments.

1-3. MS and MS/MS Analyses

The above-obtained SPITC-derivatized peptide was incorporated into 100 μl of an aqueous solution of 0.1% TFA and 90% acetonitrile. This solution was collected into a syringe and was injected at the rate of 20 μl/hr for MS and MS/MS experiments. A quadrupole ion trap mass spectrometer (QIT-MS, Model LTQ, ThermoFinnigan) was employed as the mass spectrometer. In order to precisely adjust the position of the spray-emitting part with respect to the inlet of the desolvation tube, the mass spectrometer was equipped with a self-fabricated nano electrospray ionization interface having an optical xyz-translational stage (460A series, Newport). Voltage of 2 kV was applied to the union to generate electrospray and collision-induced dissociation (referred to as CID hereinafter) energy was adjusted to 25%. In the MS/MS experiment, an isolation width of m/z=15 Da was applied for simultaneously performing CID for two ionic species.

Figure 2:
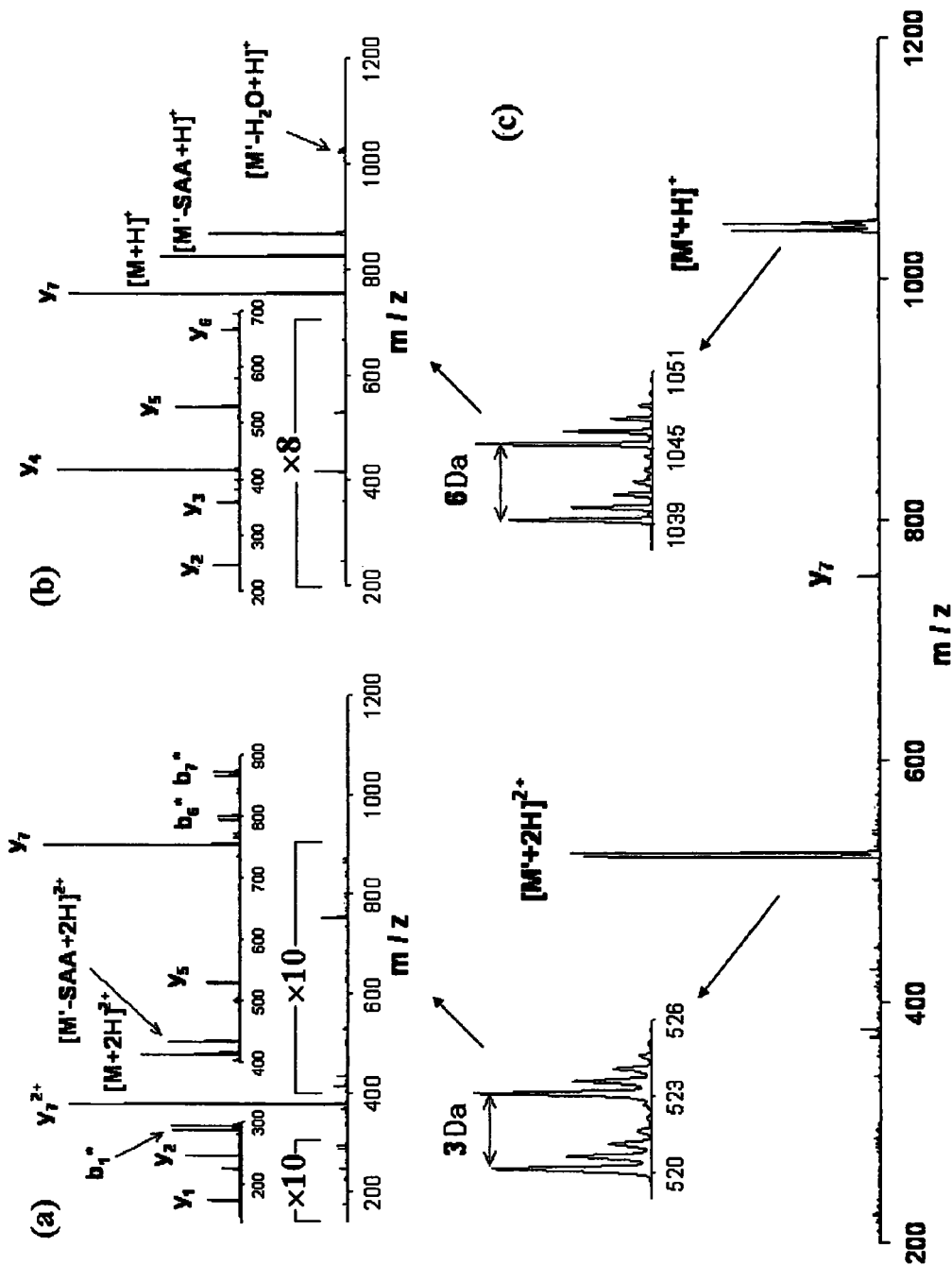
FIG. 2 shows an MS spectrum and MS/MS spectra in accordance with Preparative Example 1 of the present invention.

FIG. 2 shows the mass spectrum results thus obtained. M represents the oligo peptide (ASHLGLAR), and M' represents the oligo peptide in which the N-terminus was substituted with SPITC (SPITC-ASHLGLAR). [M'+H]$^+$, with a +1 charge, appears as a doublet with the peaks of the nearly the same intensity 6 Da apart, and the heavier species corresponds to the $^{13}$C-SPITC-derivatized oligo peptide. Similarly, for [M'+2H]$^{2+}$, with a +2 charge, the same result also appears in FIG. 2c, in which the $^{13}$C-SPITC-derivatized oligo peptide peak appears at the position where the m/z value is greater by 3. This difference in the m/z value can be observed more clearly in the zoom scan mass spectrum shown in the inset. Meanwhile, y$_7$ in the spectrum in FIG. 2c is believed to be an Edman-degraded product of in-source degradation.

As can be seen from FIG. 2, unreacted oligo peptides were not observed in any charge state and it was confirmed that $^{12}$C-SPITC and $^{13}$C-SPITC quantitatively react.

FIG. 2b shows the MS/MS spectrum for [M'+H]$^+$ and the inset is an 8-fold enlarged version of the spectrum for fragments except for y$_7$. y$_7$ is an Edman degradation product, having the strongest intensity, and peaks on the left side of y$_7$ are from backbone cleavage products, i.e. daughter ions. Since these peaks have weaker intensities compared to that of y$_7$, it can be seen that the backbone cleavage is not a primary degradation pathway, and that it occurs mostly as the result of collisions with helium atoms.

In FIG. 2b, [M'–H$_2$O+H]$^+$, [M'–SAA+H]$^+$, and [M+H]$^+$ are the species from which H$_2$O, sulfanilic acid, and SPITC were dissociated from [M'+H]$^+$, respectively. Although barely visible, the [M'–H$_2$O+H]$^+$ ion on the rightmost side of the spectrum appears as a doublet, while the other species appear as singlets only, indicating that the b-type ions are all neutral and therefore are not detected. That is, all peaks on the left side of y$_7$ are y-type ions, thereby significantly simplifying peak assignments, and each spacing between two adjacent peaks correspond to the mass of an amino acid, with the sequence identified by calculating the mass differences starting from the rightmost peak to the left.

FIG. 2a shows the MS/MS spectrum for [M'+2H]$^{2+}$, with the insets clearly showing b-type and y-type ions. The Edman-degraded product y$_7^{2+}$ ion (y$_{n-1}^{2+}$) is the most dominant species in the spectrum, while b$_1$* (SPITC-b$_1$) and y$_7$ (y$_{n-1}$) ions also show strong intensities. Other b-type and y-type ions are present as well but with lower intensities. The b-type ions have $^{12}$C-SPITC and $^{13}$C-SPITC at their N-termini and thus appear as doublets with a 6-Da difference in the mass between two ions, while y-type ions appear as singlets only.

In conclusion, in accordance with the present invention, the respective spacing between adjacent peaks in the MS/MS spectra for the SPITC-oligo peptide with a +1 charge correspond to the mass of one amino acid, and thus it is possible sequence the amino acids de novo and obtain additional information from the MS/MS spectra for SPITC-oligo peptide having a +2 charge.

Preparative Example 2

2-1. Preparation of Oligo Peptide Mixture Sample

In order to confirm the quantitativity of the method in accordance with the present invention for real protein samples, horse heart myoglobin was subjected to experiments. Complete degradation of the horse heart myoglobin by treatment of trypsin produces 21 kinds of oligo peptides. 10 μg of myoglobin was dissolved in 60 μl of 100 mM NH$_4$HCO$_3$ buffer, and denatured at 90° C. for 10 min. Then, this solution was cooled to the room temperature and 40 μl of methanol and 200 ng of trypsin were added (50:1 protein to enzyme), followed by degradation at 37° C. for 15 min. The oligo peptide sample was thoroughly dried using a SpeedVac Concentrator (Thermo Savant) and stored at −20° C. for subsequent experiments.

2-2. Derivatization of Oligo Peptide

Assuming that the above-obtained oligo peptide (B) has an average molecular weight of 800 Da and the total number of moles of the oligo peptide derived from 10 μg of myoglobin is 12.5 nmol, derivatization of oligo peptide was carried out using the same procedure as in Preparative Example 1-2.

2-3. cRPLC/MS/MS Analysis

The above-obtained SPITC-derivatized oligo peptide mixture was dissolved in 50 μl of an aqueous solution of 0.05% TFA and 0.2% acetic acid and 5 μl of this solution (about 1 μg of the oligo peptide mixture) was injected into the sample loop of the self-fabricated liquid chromatography (capillary RPLC) system and then loaded onto a column. As the mass spectrometer, the quadrupole ion trap mass spectrometer (QIT-MS, Model LTQ, ThermoFinnigan) was used which was equipped with a self-fabricated nano electrospray ionization interface that was employed in Preparative Example 1. In order to precisely adjust the location of a spray emitter relative to a desolvation tube, an optical xyz-translational stage (460A series, Newport) was adopted as the interface. In addition, the interface was designed to minimize dead space between LC and mass spectrometer by directly connecting the separation column to the electrospray emitter using a stainless steel conjugation tube. Voltage of 2 kV was applied to the conjugation tube so as to generate electrospray. The above-mentioned liquid chromatography was an ultra pressure RPLC system, and mobile phases (solvent X: aqueous solution of 0.05% TFA and 0.2% acetic acid, solvent Y: an aqueous solution of 0.1% TFA and 90% acetonitrile) was allowed to be delivered under pressure of 10,000 psi, using two ISCO syringe pumps (Model 100DM, manufactured by ISCO). The mobile-phase solvents were homogeneously mixed in a stainless steel mixer using a magnetic stirrer prior to passing through the packed capillary column (inner diameter: 75 μm, outer diameter: 360 μm, length: 1 m, capillary tube manufactured by Polymicro Technologies) and to the flow splitter. The column was prepared in the laboratory, using branched hydrocarbon particles (pore size: 300, and particle size: 5 μm, manufactured by Phenomenex) containing 18 carbon atoms, and the solvent Y concentration was varied with exponential gradient from 0 to 80%, for 200 min. In order to perform amino acid sequencing through mass analysis of myoglobin, QIT-MS was operated in a data-dependent tandem MS mode, which continuously performs subsequent MS/MS for two ionic species most abundantly detected in the preceding MS scan. Meanwhile, CID energy was adjusted to 35%, and the MS/MS was performed with an isolation width of m/z=15 Da for simultaneous CID of two ionic species.

Figure 3:
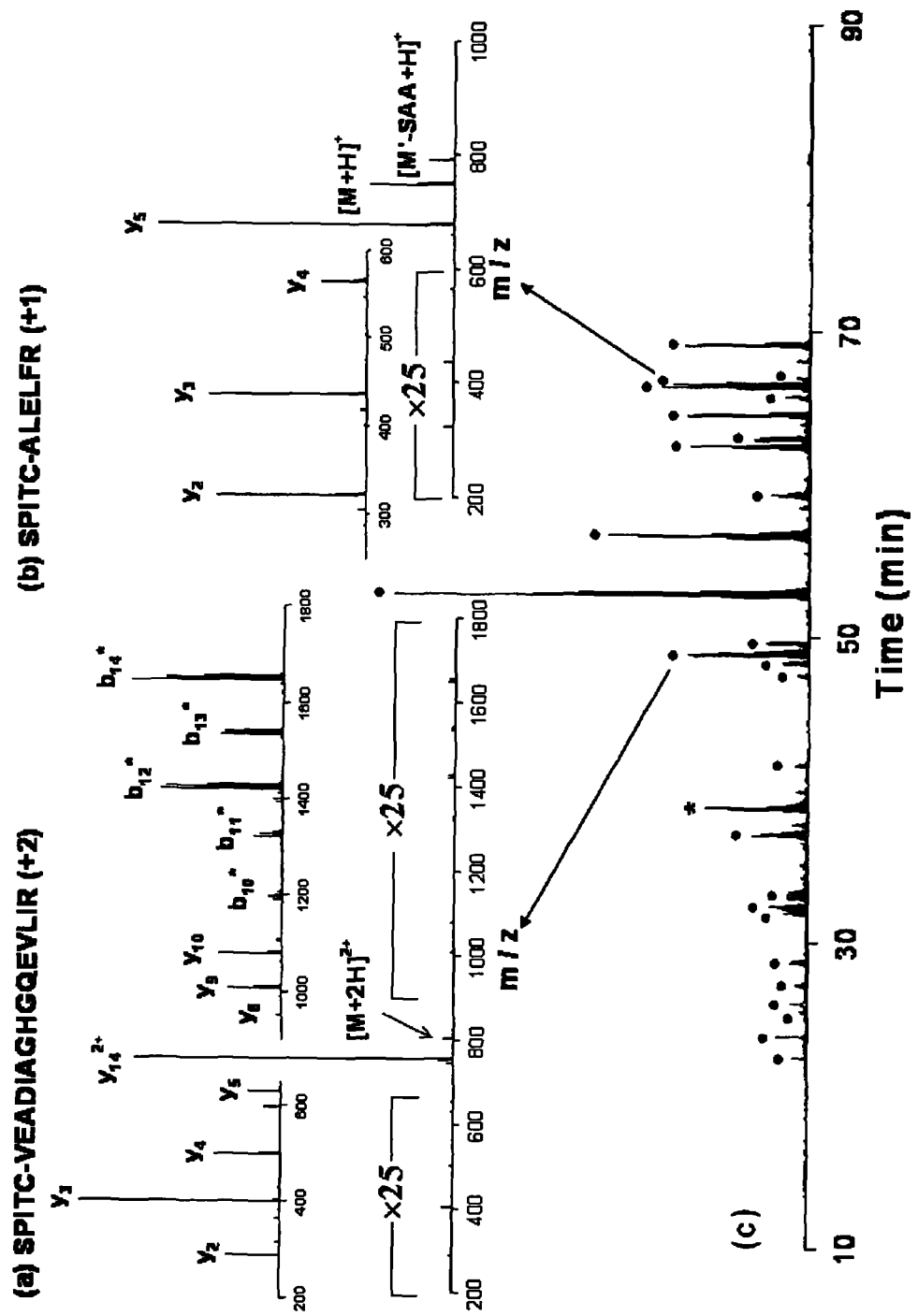
FIG. 3 shows base peak chromatogram and MS/MS spectra for a portion thereof, in accordance with Preparative Example 2 of the present invention.

FIG. 3c shows a base peak chromatogram obtained from the above-mentioned experiment, and MS/MS spectra (FIGS. 3a and 3b) of a few peaks selected from the chromatogram In FIG. 3c, the SPITC-derivatized oligo peptides appear to be well-separated. In addition, no significant peaks due to unexpected reactions are observed and only unreacted peptide appeared (marked with an asterisk). Peaks marked with circular dots correspond to the SPITC-derivatized peptides, and appear as doublets in the mass spectrum. FIGS. 3a and 3b present MS/MS spectra of the modified oligo peptides that were being eluted at the times indicated. FIG. 3a shows the MS/MS spectrum of the oligo peptides eluted about 49 min after the initiation of liquid chromatography. The doublet in the MS/MS spectrum consists of two peaks that are 3 Da apart, indicating that these peaks result from a doubly charged species. The doublet with a mass difference of 6 Da in the MS/MS spectrum indicates the presence of SPITC-b (referred to as b* hereinafter) and could be achieved using information provided by the continuous series of the b* ions, $y_{n-1}^{2+}$, and other singlets. Specifically, since the C-terminus of oligo peptides degraded by proteolytic enzymes, as previously explained, is either arginine (R) or lysine (K), and the mass difference between the heaviest b* ion, and the mass of the singly charged parent ion was 174 Da, the corresponding amino acid was confirmed to be [arginine (156 Da)+$H_2O$]. In addition, by comparing m/z differences within the doublet series (b* ions), the present inventors could assign amino acids to respective m/z values. Also, in FIG. 3a, the 113-Da mass difference between the doublets (m/z=1647.4, 1653.5 Da and m/z=1534.3, 1540.4 Da) led to the conclusion that the corresponding amino acid was either leucine (L) or isoleucine (I) (leucine and isoleucine are isomers and are indistinguishable my mass). In addition, the same mass difference (113 Da) between the above-mentioned latter doublet (m/z=1534.3, 1540.4 Da) and the adjacent left doublet (m/z, 1421.2, 1427.3 Da), implies that the next amino acid was also either leucine or isoleucine. Analogously, the inventors confirmed the presence of V (99 Da) and E (129 Da) by observing the mass differences with the doublets at n/z=1322.3, 1328.3 Da and m/z=1193.4, 1199.2 Da, respectively. In addition, in the case of the SPITC-derivatized oligo peptide with a +2 charge, considering the fact that $y_{n-1}^{2+}$ or $y_{n-1}$ peaks generally exhibit the strongest peak intensity, it was determined that the first amino acid at the N-terminal side was valine (V) by calculating the mass difference between $[M+2H]^{2+}$ and the mass corresponding to valine. From such de novo sequencing, the present inventors concluded that the oligo peptide in question was V-?--?-EVL(I)L(I)R. Next, by comparing to the protein sequence for myoglobin from a database, it was confirmed that the SPITC-derivatized oligo peptide was VEADIAGHGQEVLIR. Since it was clear that the doublet with a mass difference of 6 Da is due to a b-type ion, the occurrence of error upon comparison with the database was minimized and e various weak-intensity peaks appearing as the result of backbone cleavages were clearly identified.

Meanwhile, FIG. 3b shows the base peak chromatogram and MS/MS spectrum obtained for the doublet (m/z=963.5, 969.5 Da) appearing at around 66 min in the base peak chromatogram, and the peaks in the doublet are 6 Da apart in the MS/MS spectrum. Sequencing the peptide de novo, the mass difference of the peaks at m/z=748.4 and 677.4 Da, which correspond to the protonated peptide mass and the Edman-degraded product, show that the amino acid at the N-terminus is alanine (A, 71 Da). Likewise, the second amino acid from the N-terminus is either leucine or isoleucine (677.4 Da−564.3 Da=113 Da), and the third and fourth are glutamic acid (564.3 Da−435.3 Da=129 Da) and either leucine or isoleucine (435.3 Da−322.2 Da=113 Da), respectively. This oligo peptide is a tryptic peptide, so the C-terminal amino acid must be either arginine or lysine. First, assuming that the C-terminal amino acid is arginine, it can be said that the peak at m/z=322.2 Da in FIG. 3b is from XR, and the mass difference between this peak and that arising from the C-terminal arginine (145 Da (arginine)+19 Da ($H_3O^+$)=175 Da) is 147 Da. Since no two amino acids may have a combined mass of 147 Da, X corresponds one amino acid only, and the present inventors determined its mass coincides with that of phenylalanine (F, 147 Da). However, if one assumes that the C-terminal amino acid is lysine and the amino acid sequence at the C-terminus is XK, the difference between the mass of this peak and that of the cC-terminal lysine (128 Da (lysine)+19 Da ($H_3O^+$)=147) is 175 Da. Since m/z=175 Da is consistent with neither the mass of any amino acid nor the combined mass of any two amino acids, lysine cannot be at the C-terminus of the oligo peptide. Therefore, the present inventors confirmed that the oligo peptide was AL(I) EL(I)FR. Comparing this sequence with the protein sequence of myoglobin in the database, it was confirmed that the SPITC-derivatized oligo peptide was ALELFR of myoglobin. Again referring to FIG. 3b the peak ($y_5$) generated by Edman degradation appears with the strongest intensity, and the peaks $[M+H]^+$ and $[M'-SAA+H]^+$, which are the oligo peptide derivatives from which SPITC and sulfanilic acid are dissociated, respectively, and other y-type ions generated by backbone cleavages are apparent. In addition, MS/MS spectra for all other derivatized oligo peptides shown in the base peak chromatogram in FIG. 3c exhibit the same patterns as observed in the representative spectra presented in FIGS. 3a and 3b.

Meanwhile, MS data and MS/MS data obtained from cRPLC (capillary-RPLC)/MS/MS experiments were analyzed using a commercially available search program, SEQUEST, and through amino acid sequence information of myoglobin protein, available from NCBI (http://www.ncbi.nih.gov). In this connection, based on the assumption that the N-termini of all of oligo peptides derived from myoglobin were derivatized with $^{13}$C-SPITC, $^{13}$C-SPITC-derivatized oligo peptides were first searched and identified. Next, using the quantitative analysis program XPRESS (System Biology), the peaks ($^{12}$C-SPITC-derivatized oligo peptides) that are 6 Da smaller in mass than those respective $^{13}$C-SPITC-derivatized oligo peptides were searched to obtain relative quantitative data. Differences in elution time between $^{13}$C-SPITC-derivatized chemical species and $^{12}$C-SPITC-derivatized species, and their quantified values are shown in Table 1 below.

TABLE 1

| Oligo peptide of myoglobin | Difference in elution time | $^{13}$C/$^{12}$C (Abundance ratio) |
|---|---|---|
| GLSDGEWQQVLNVWGK | 0 | 0.94 |
| VEADIAGHGQEVLIR | 0.02 | 1.02 |
| HGTVVLTALGGILK | 0.02 | 1.01 |
| ALELFR | 0 | 1.03 |
| TEAEMK | 0 | 0.99 |
| ASEDLK | 0 | 1.04 |
| ELGFQG | 0.01 | 0.92 |
| FDK | 0.02 | 0.99 |
| HLK | 0.01 | 1.03 |
| FK | 0 | 0.98 |
| ALELFRNDIAAK | 0 | 1.01 |
| YKELGFQG | 0 | 0.95 |

TABLE 1-continued

| Oligo peptide of myoglobin | Difference in elution time | $^{13}C/^{12}C$ (Abundance ratio) |
|---|---|---|
| ASEDLKK | 0.01 | 1.05 |
| FDKFK | 0.01 | 1.01 |

As presented in Table 1, the two isotope-substituted species have almost the same elution time and exhibit excellent quantitativity.

Example 2

2-1. Preparation of Oligo Peptide Mixture Sample

In order to perform 1:1 quantitative test and de novo sequencing test for two real protein samples, 100 μg of the two identical yeast enolase samples C and D were degraded (complete degradation with trypsin produces 52 types of oligo peptides) using the same procedure described in Preparative Example 2-1, and then were thoroughly dried using a SpeedVac Concentrator (Thermo Savant) and stored at −20° C. for subsequent experiments.

2-2. Derivatization of Oligo Peptide

Under the assumption that the above-mentioned oligo peptides (C and D) have an average molecular weight of 800 Da, respectively, derivatization of oligo peptides was carried out by preparing and using stock solutions of $^{13}$C-SPITC and $^{13}$C-SPITC, in which 1 mg of each of $^{12}$C-SPITC and $^{13}$C-SPITC prepared in Example 1 was dissolved in 200 μl of a 1:1:2 pyridine/water/ethanol solution shortly prior to use. Derivatization of oligo peptides was carried out using the same procedure described in Preparative Example 1-2, except that for derivatization of samples C and D, $^{12}$C-SPITC and $^{13}$C-SPITC were used, respectively. Each product was incorporated into 100 μl of an aqueous solution of 0.05% TFA and 0.2% acetic acid, and then 0.5 μl of each was mixed together to prepare a 1:1 (v/v) mixed solution. Then, 4 μl of an aqueous solution of 0.05% TFA and 0.2% acetic acid was added to make the total volume 5 μl and the mixture was stored at −20° C. for subsequent experiments.

2-3. RPLC/MS/MS Analysis

Figure 4:
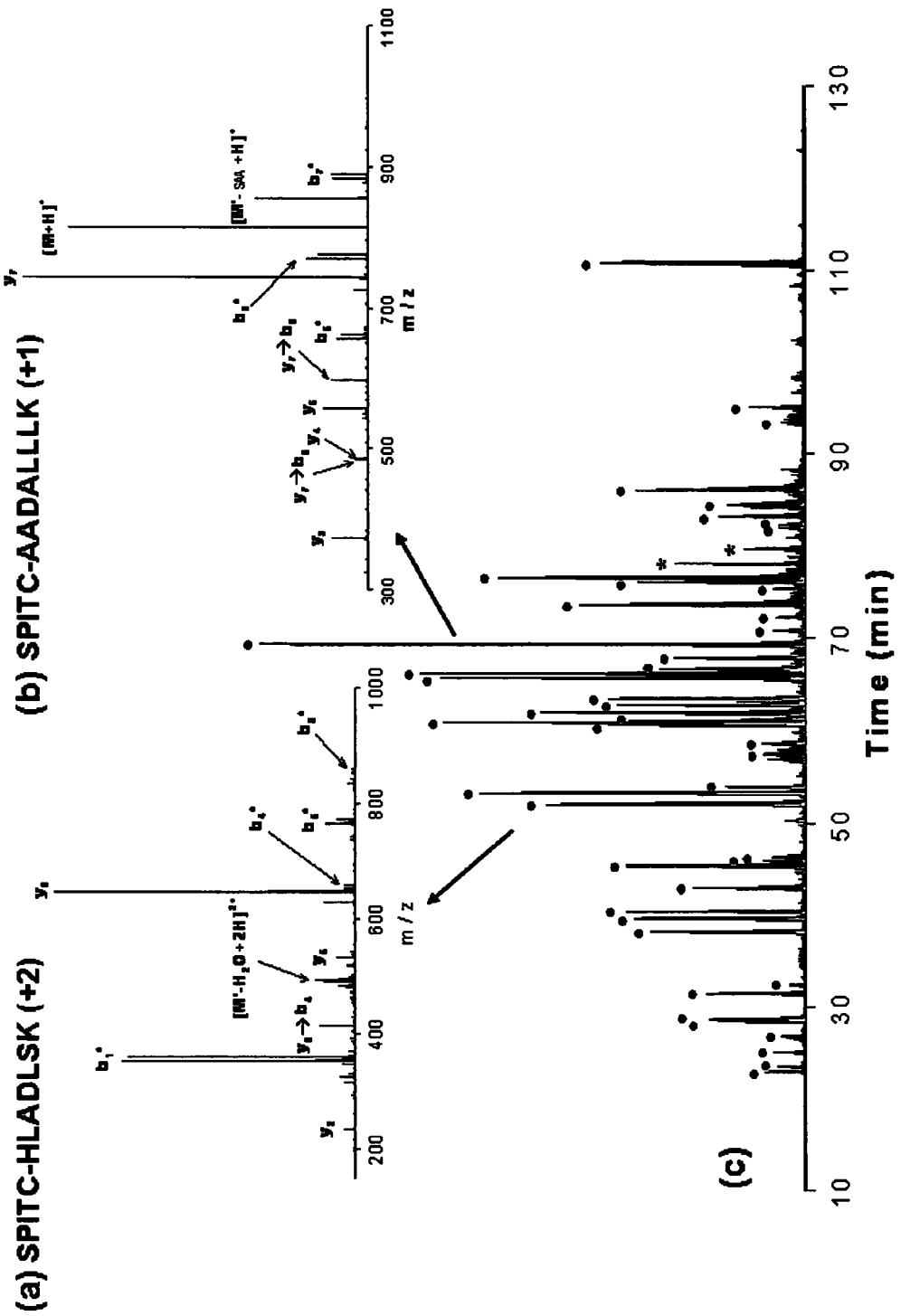
FIG. 4 shows a base peak chromatogram and MS/MS spectra for a portion thereof, in accordance with Example 2 of the present invention.

RPLC/MS/MS experiments were carried out for the above-prepared derivatized sample C and D mixture (1:1 v/v) using the same procedure described in Preparative Example 2-3. FIG. 4c shows the base peak chromatogram obtained with the above-mentioned experiments, together with MS/MS spectra of a few selected peaks from the above chromatogram.

In FIG. 4c, it can be seen that the SPITC-derivatized oligo peptides appear well-separated. In addition, no significant peaks as the result of unexpected reactions were observed and two unreacted peptide peaks are present. Peaks marked with circular dots in FIG. 4c correspond to the peptides derivatized by SPITC, and appear as doublets in the mass spectrum. Peaks marked with a asterisks represent unreacted oligo peptides.

Meanwhile, FIG. 4a shows the MS/MS spectrum of the doublet that appears at around 52 minutes in the base peak chromatogram, exhibiting a difference of 3 Da in m/z values in the mass spectrum. The 3-Da mass difference indicates that the doublet correspond to a peptide with a +2 charge. It can be predicted that the relatively more intense peaks appearing as a doublet with a difference of 6 Da in the MS/MS spectrum is $b_1$*, indicating that the first amino acid of this peptide is histidine. This result can be further clarified by identification of $y_{n-1}$ ion, which is a conjugate ion of $b_1$*. Next, comparing to the protein sequence database for yeast, it was confirmed that the SPITC-derivatized oligo peptide was a tryptic peptide of enolase, HLADLSK. It was apparent that the doublet with a mass difference of 6 Da is a b-type ion, minimizing possible occurrences of errors when compared to the database, clearly identifying various low-intensity peaks as the result of backbone cleavages.

In addition, FIG. 4b shows the MS/MS spectrum of the 6-Da mass-difference doublet (m/z=1029.5, 1035.4 Da) arising from the oligo peptide being eluted at about 69 min after the initiation of elution. Based on the observation that the mass difference between the most intense doublet (m/z=883.0, 889.1 Da; confirmed as $b_7$*) and the parent ion peak is 146 Da (128 Da (lysine)+18 Da ($H_2O$)=146 Da), one can conclude that the C-terminus of this oligo peptide is lysine. A mass difference of 113 Da between the $b_7$* peak and the doublet (m/z=770.1, 776.0 Da; confirmed as $b_6$*) indicates that the amino acid next to lysine was either leucine or isoleucine. Similarly, the next amino acid was also either leucine or isoleucine. Thus, a sequence of L(I)L(I)K at the C-terminal side was obtained and the doublet at m/z=814.4 Da in FIG. 4b corresponds to [M+H]$^+$ in which $^{13}$C-SPITC (221 Da) or $^{12}$C-SPITC (215 Da) was dissociated from the parent ion. Another intense peak (confirmed as $y_7$) at m/z=743.3 Da is from a species produced by Edman degradation. Since the mass difference between this ion and [M+H]$^+$ is 71 Da, the amino acid at the N-terminus is alanine. Also, there is a 146-Da mass difference between the Edman-degraded product and the ion at m/z=597.3 Da. There is no amino acid with this mass value and since lysine is at the C-terminus of the SPITC-derivatized oligo peptide, the peak in question most likely results from a b-type ion product from by an internal fragmentation. Specifically, it could be seen that the $y_{n-1}$ ion results from a b-type ion (confirmed as $y_7 \rightarrow b_6$) in which lysine at the C-terminal side (128 Da (lysine)+18 Da ($H_2O$)=146 Da) was dissociated from the Edman-degraded product (confirmed as $y_7$) formed via a secondary degradation process. Also, an additional loss of leucine results in the $y_7 \rightarrow b_5$ peak that appears 113 Da to the left of the $y_7 \rightarrow b_6$ peak, and the $y_3$ ion (protonated L(I)L(I)K) is also present at m/z=373.2 Da. Next, the mass difference between the m/z=486.3 Da peak ($y_4$ ion; this ion is only 2 Da lighter than the $y_7 \rightarrow b_6$ ion so these two are not isotope-related) and the $y_3$ ion is 113 Da, which is the mass of leucine and isoleucine, and therefore, the sequence is L(I)L(I)L(I)K. The presence of a peak at m/z=557.4 Da indicates that the next amino acid is alanine (71 Da) and so by de novo sequencing, this oligo peptide has the sequence of A-?--?-AL(I)L(I)L(I)K. "-?--?-" refers to species with m/z=186 Da and could be AD (71 Da (alanine)+115 Da (asparaginic acid)=186 Da) or DA, GE (57 Da (glycine)+129 Da (glutamic acid)=186 Da) or EG, VS (99 Da (valine)+87 Da (serine)=186 Da) or SV, or W (tryptophan, 186 Da). Finally, by comparing the above results with the protein sequence database of yeast, it was confirmed that "-?--?-" corresponds to AD and the complete oligo peptide sequence is AADALLLK. In short, FIG. 4b shows that the makor peaks correspond to [M−H]$^+$ and [M′−SAA+H]$^+$, produced when SPITC and sulfanilic acid were dissociated from the modified oligo peptide, respectively, and the $y_7$ ion. Backbone cleavages produce other y-type ions, and the high-mass b* ions are also detected. The latter are easily identified because they appear as doublets with peaks 6 Da apart, and their presences may be explained by the possibility that their proton affinities are greater than those of the light-mass y-type ions. Particularly, since the C-terminal amino acid of the derivatized oligo peptide is lysine and has a lower proton affinity than arginine, b* type ions are more likely to be formed and detected.

In addition, the MS/MS spectra for all other derivatized oligo peptides in the chromatogram exhibit the same patterns as those two representative spectra shown above, and about 95% of the amino acid sequence of enolase was analyzed, in accordance with the present invention.

Example 3

3-1. Preparation of Oligo Peptide Mixture Sample

An oligo peptide sample for yeast enolase was prepared using the same procedure described in Example 2-1.

3-2. Derivatization of Oligo Peptide

Derivatization of the oligo peptides (C and D) above was carried out using the same procedure described in Example 2-2. Each product was mixed with 100 μl of an aqueous solution of 0.05% TFA and 0.2% acetic acid, and appropriate amounts of the sample D solution were added to the fixed volume (0.5 μl) of the sample C solution to achieve volume ratios of 1:1, 1:2, 1:4, 1:6, 1:8, and 1:10. Then, an aqueous solution of 0.05% TFA and 0.2% acetic acid was added to adjust the volume of the mixed solution to 5 μl and the mixed solution was then stored at −20° C. for subsequent experiments.

3-3. cRPLC/MS/MS Analysis

Figure 5:
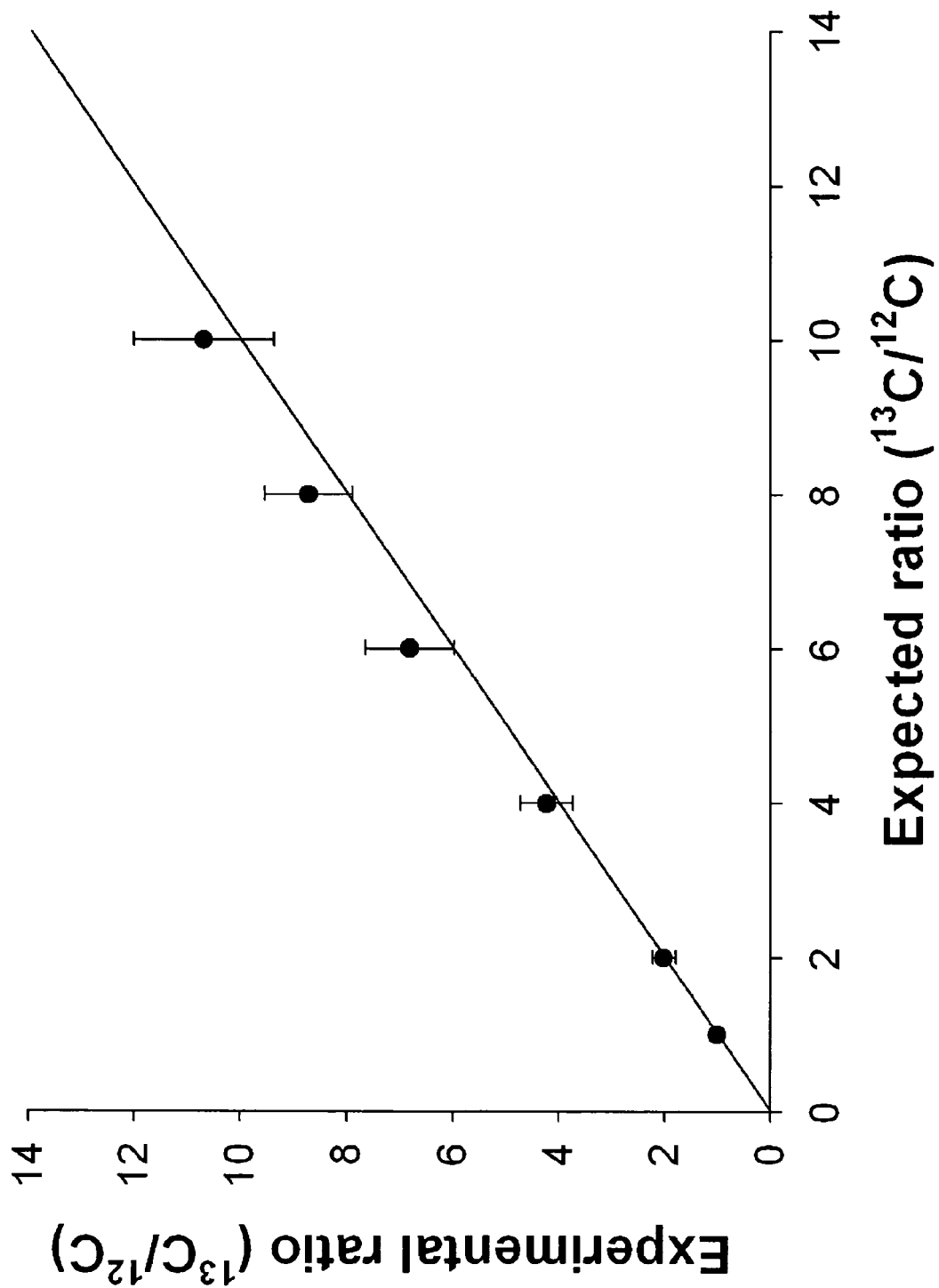
FIG. 5 shows a graph of the measured quantitativity in accordance with a method of the present invention while varying an oligo peptide ratio according to Example 3 of the present invention.

Following the procedure described in Preparative Example 2-3, 6 cRPLC/MS/MS experiments were carried out for the 1:1, 1:2, 1:4, 1:6, 1:8 and 1:10 mixtures of the derivatized samples C and D, and results similar to the example were obtained. In order to quantify these examples, under the assumption that all of the tryptic oligo peptides in the database were derivatized with $^{13}$C-SPITC, the $^{13}$C-SPITC-derivatized oligo peptides were first searched using a commercially available database search program SEQUEST. Identification results were obtained based on the search process and these results were used to run a quantitative analysis program, XPRESS (System Biology) to identify the peaks ($^{12}$C-SPITC-derivatized oligo peptides) exhibiting a mass difference of −6 Da compared to the above peptide peak, and obtained relative quantitative data. From these results, quantified values were obtained for about 30 oligo peptides per experiment. The average values and standard deviations of the quantified values were calculated and listed in Table 2. FIG. 5 shows a plot of the measured values versus expectation values using the results in Table 2.

TABLE 2

| Expected value | Measured value | Standard deviation | Standard deviation (%) |
|---|---|---|---|
| 1 | 1.01 | 0.06 | 5.9 |
| 2 | 2.02 | 0.22 | 10.9 |
| 4 | 4.24 | 0.49 | 11.6 |
| 6 | 6.83 | 0.84 | 12.3 |
| 8 | 8.73 | 0.81 | 9.3 |
| 10 | 10.70 | 1.32 | 12.3 |

As shown in Table 2 and FIG. 5, all of the cRPLC/MS/MS experiments exhibited only about 10% deviation from average values and thus, relatively accurate quantitative results were obtained.

As described above, the reagent for N-terminal substitution in the present invention reacts only with amino groups in the backbone but not with the epsilon-amino group of lysine, exhibiting excellent quantitativity. Furthermore, in accordance with the present invention, the method for sequencing and quantifying amino acids can perform a relative quantitative analysis of proteins with very high reliability, and y-type ions can be accurately distinguished from b-type ions by means of tandem mass spectrometry, enabling realization of high-reliability protein identification.

Although the present invention has been only partially disclosed for illustrative purposes, those skilled with the experiment will appreciate that various modifications, additions and substitutions are possible without departing from the scope and spirit of the invention as disclosed in the accompanying claims.

The invention claimed is:

1. A method for sequencing and quantifying amino acids in a sample of polypeptides, comprising:
    dividing the sample of polypeptides into a first polypeptide sample and a second polypeptide sample;
    separately degrading each of the first polypeptide sample and the second polypeptide sample using proteolytic enzymes to form a first degraded oligo peptide mixture and a second degraded oligo peptide mixture, wherein the C-terminus of each degraded oligo peptide of the first and second oligo peptide mixtures is arginine or lysine;
    derivatizing the first degraded oligo peptide mixture having arginine or lysine at the C-terminus with a compound for N-terminal substitution containing $^{12}$C, and derivatizing the second degraded oligo peptide mixture with a compound for N-terminal substitution containing $^{13}$C, wherein the compound for N-terminal substitution containing $^{12}$C is a compound represented by Formula 3, and the compound for N-terminal substitution containing $^{13}$C is an isotope of the compound for N-terminal substitution containing $^{12}$C, in which each $^{12}$C of the phenyl ring in the compound of Formula 3 is replaced by $^{13}$C;

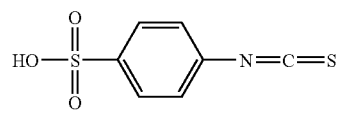

Formula 3 mixing the first derivatized oligo peptide mixture and the second derivatized oligo peptide mixture to form a third mixture;
    separating the third mixture with Reverse-Phase Liquid Chromatography to form a separated third mixture;
    obtaining a base peak chromatogram and MS/MS spectra of the separated third mixture using a mass spectrometer; and
    interpreting the obtained spectral results of the separated third mixture.

2. The method as set forth in claim 1, wherein the proteolytic enzyme is trypsin, endoproteinase Lys C or endoproteinase Arg C.

3. The method as set forth in claim 1, wherein the proteolytic enzyme is trypsin.

4. The method as set forth in claim 1, wherein the mass spectrometer is a Matrix-Assisted Laser Desorption/Ionization (MALDI) type mass spectrometer.

5. The method as set forth in claim 1, wherein the mass spectrometer is an Electro Spray Ionization (ESI) type mass spectrometer and is directly connected to a reverse-phase liquid chromatograph (RPLC).

6. The method as set forth in claim 1, wherein the derivatizing the first degraded oligo peptide mixture and the derivatizing the second degraded oligo peptide mixture are each carried out at a pH in the range of 7 to 9.

7. The method as set forth in claim 1, wherein at least one of the first degraded oligo peptide mixture and the second degraded oligo peptide mixture has lysine at the C-terminus, and wherein the derivatizing comprises derivatizing the N-terminus of the lysine while keeping the $\epsilon$-amino group of the lysine intact.

8. The method as set forth in claim 1, wherein the interpreting the obtained spectral results of the separated third mixture comprises using commercially available software programs or databases.

\* \* \* \* \*

UNITED STATES PATENT AND TRADEMARK OFFICE
CERTIFICATE OF CORRECTION

PATENT NO. : 8,501,488 B2  Page 1 of 1
APPLICATION NO. : 11/630625
DATED : August 6, 2013
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1965 days.

Signed and Sealed this
Fifteenth Day of September, 2015

Michelle K. Lee
*Director of the United States Patent and Trademark Office*